(12) United States Patent
Goldberg

(10) Patent No.: US 6,997,909 B2
(45) Date of Patent: Feb. 14, 2006

(54) LOW PROFILE COMBINATION DEVICE FOR GASTROSTOMY OR JEJUNOSTOMY APPLICATIONS HAVING ANTI-GRANULOMA FORMATION CHARACTERISTICS

(75) Inventor: Elizabeth A. Goldberg, West Chester, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 41 days.

(21) Appl. No.: 10/420,450

(22) Filed: Apr. 22, 2003

(65) Prior Publication Data

US 2004/0024363 A1    Feb. 5, 2004

Related U.S. Application Data

(60) Provisional application No. 60/374,401, filed on Apr. 22, 2002, provisional application No. 60/374,537, filed on Apr. 22, 2002.

(51) Int. Cl.
*A61M 5/32* (2006.01)

(52) U.S. Cl. .............. 604/175; 604/102.02; 604/104; 604/910

(58) Field of Classification Search ............ 604/93.01, 604/96.01, 117, 103, 174, 175, 104, 102.02, 604/910; 606/192
See application file for complete search history.

(56) References Cited

U.S. PATENT DOCUMENTS

| | | | |
|---|---|---|---|
| 4,311,148 A | 1/1982 | Courtney et al. | |
| 4,666,433 A * | 5/1987 | Parks | 604/178 |
| 4,685,901 A | 8/1987 | Parks | |
| 4,863,438 A | 9/1989 | Gauderer et al. | |
| 5,098,378 A | 3/1992 | Piontek et al. | |
| 5,151,086 A | 9/1992 | Duh et al. | |
| D350,393 S | 9/1994 | Potter | |
| 5,512,055 A * | 4/1996 | Domb et al. | 604/265 |
| 5,527,280 A | 6/1996 | Goelz | |
| 5,902,285 A | 5/1999 | Kudsk et al. | |
| 6,045,536 A | 4/2000 | Meier et al. | |
| 6,063,396 A | 5/2000 | Kelleher | |
| 6,287,281 B1 | 9/2001 | Nishtala et al. | |
| 6,322,538 B1 | 11/2001 | Elbert et al. | |
| 6,328,720 B1 | 12/2001 | McNally et al. | |

(Continued)

FOREIGN PATENT DOCUMENTS

EP    1 297 848 A1    4/2003

OTHER PUBLICATIONS

Ballard Medical Products, Kimberly-Clark MIC Enteral Feeding Tubes and Accessories.

(Continued)

*Primary Examiner*—Kevin C. Sirmons
(74) *Attorney, Agent, or Firm*—Caesar, Rivise, Bernstein, Cohen & Pokotilow, Ltd.

(57) ABSTRACT

A combination device for gastrostomy or jejunostomy usage having a retaining member, an elongated member having a gastrostomy lumen and a jejustomy lumen, and an inflatable balloon mounted on the elongated member. The retaining member is of a low profile and is arranged to be located on the skin adjacent a stoma in the abdominal wall through which the elongated member extends. The balloon seals the stoma about the elongated member. The retaining member includes at least one access port to communicate with respective ones of the lumens. The device, related compositions, and processes can prevent and/or treat granulomas.

26 Claims, 3 Drawing Sheets

U.S. PATENT DOCUMENTS

| | | |
|---|---|---|
| 6,497,729 B1 | 12/2002 | Moussy et al. |
| D471,640 S | 3/2003 | McMichael et al. |
| 6,527,748 B1 | 3/2003 | Suzuki |
| 2003/0045841 A1 | 3/2003 | Palcisko et al. |

OTHER PUBLICATIONS

Robbins, Pathologic Basic of Disease, 5$^{th}$ Edition, Copyright 1994.

* cited by examiner

LOW PROFILE COMBINATION DEVICE FOR GASTROSTOMY OR JEJUNOSTOMY APPLICATIONS HAVING ANTI-GRANULOMA FORMATION CHARACTERISTICS

BACKGROUND OF THE INVENTION

1. Field of Invention

The invention relates generally to medical devices and more particularly to a low profile device including respective gastrostomy and jejunostomy lumens allowing both gastric and jejunal access. The invention further relates to compositions for coating such devices to prevent or treat granulomas.

2. Description of Related Art

There are many patients who are unable to orally receive nutrition due to physical or physiologic conditions caused by diseases or other maladies. People suffering from stroke, Alzheimer's disease, cancer, inflammation, or other infirmities, often cannot properly chew, swallow or absorb their food or medication, which must then be delivered to the patient in another fashion if starvation and malnutrition are to be avoided.

Gastrostomy/jejunostomy tubes have become the method of choice in providing long-term nutritional support to children and adults. Gastrostomy/jejunostomy tubes may either be placed through the surgical creation of an ostomy while the patient is under general anesthesia or by means of percutaneous endoscopic gastrostomy (PEG) or by percutaneously radiographically placed gastrostomy, which involves a non-invasive creation of an opening or stoma in the stomach through the abdominal wall.

There are often instances in which it is preferable to introduce the patient's nutritional requirements in the form of a liquid formula to the jejunum portion of the small intestine rather than the stomach. Some patients for example, when fed directly to the stomach, encounter a problem with such delivery known as reflux. In reflux, digested gastric residue is vomited up out the stomach and into the esophagus. Chronically ill or bed-ridden patients who are unable to swallow normally may inadvertently inhale the gastric reflux into the lungs resulting in asphyxiation or pneumonia. The tube itself can be forced out of the stomach as well. These situations in particular call for jejunal delivery of the nutritional formula.

It has been found in these instances that more efficacious feeding can be achieved if the feeding tube is passed through the pyloric area, and formula is passed directly into the patient's small intestine via a jejunostomy tube, rather than the patient's stomach. It has been further noted that when the feeding tube is installed so that the distal end is past the patient's pyloric valve, the tendency for the tube to be refluxed up to the esophagus is significantly reduced.

The jejunal feeding tube (a J-tube) is introduced either through a surgically created ostomy or through the nasopharyngeal passageway. A J-tube can also be placed directly through the stomach (gastrostomy), passing through the pyloris directly into the midsection of the small bowels (jejunal).

The combination of a gastrostomy and jejunostomy tube has been used for transpyloric feeding with the ability to vent the stomach. Various patents disclose gastrostomy device and/or jejunostomy devices. See for example, U.S. Pat. No.: 6,328,720 (McNally et al.); U.S. Pat. No. 5,871,467 (Reuning et al.); U.S. Pat. No. 5,549,657 (Stern, et al.); U.S. Pat. No. 5,411,491 (Goldhardt, et al.); U.S. Pat. No. 5,391,159 (Hirsch, et al.); U.S. Pat. No. 5,356,391 (Stewart); U.S. Pat. No. 5,342,321 (Potter); U.S. Pat. No. 5,336,203 (Goldhardt, et al.); U.S. Pat. No. 5,080,650 (Hirsch, et al.); U.S. Pat. No. 4,861,334 (Nawaz); U.S. Pat. No. 4,850,953 (Haber, et al.), and U.S. Pat. No. 3,915,171 (Shermata).

Typical conventional gastrostomy and jejunostomy devices commercially available today extend about 6 to 8 inches from the patient's torso and are heavy. Their relatively large size and weight renders them less than optimal insofar as comfort and concealability is concerned. Moreover, such large and heavy devices are particularly unsuitable for pediatric usage. Low profile gastrostomy and jejunostomy devices are disclosed in U.S. Pat. No.: 6,287,281 (Nishtala); U.S. Pat. No. 6,045,536 (Meier et al.) and U.S. Pat. No. 4,863,436 (Gauderer et al.) and U.S. Design Letters Patent No. D350,393 (Potter) and one such device is commercially available from Kimberly-Clark Corp (Dallas, Tex.) under the trade designation KIMBERLY-CLARK MIC Transgastric-Jejunal Feeding Tubes. That device basically comprises a tube for jejunal feeding with multiple feeding exit ports, a jejunal feeding port, a tube for gastric decompression with multiple gastric ports, a gastric decompression port, and an inflatable internal retention balloon. The jejunal feeding port and the gastric decompression port are made at the respective angles of approximately 90° and 45°. Disadvantages of this device include uneven flow and possible clogging due to its geometry.

Another disadvantage of prior art gastrostomy and jejunostomy devices is their tendency to produce undesirable granuloma tissue at the stoma site, particularly under long-term use conditions.

Thus, it is desirable to provide an improved gastrostomy/jejunostomy device that is capable of allowing both gastric access and jejunal access, which is light weight, has a low external profile, prevents or lessens the formation of granulomas at the stoma, and is capable of use in pediatric medicine.

All references cited herein are incorporated herein by reference in their entireties.

BRIEF SUMMARY OF THE INVENTION

In accordance with this invention, there is provided a combination device for gastrostomy or jejunostomy usage. The device basically comprises a retaining member, an elongated member and an activatable sealing member. The elongated member has a distal portion having a longitudinal axis. The elongated member is secured to the retaining member at the distal portion and comprises a first lumen and a second lumen. The sealing member, e.g., an inflatable balloon, is mounted on the elongated member. The retaining member is arranged to be located on the skin of a living being adjacent a stoma in the abdominal wall of the being and has a low profile with respect to the being's skin. The retaining member includes at least one access port.

The elongated member extends from the retaining member and is arranged to pass through the stoma so that the first lumen can serve as a gastrostomy tube and the second lumen can serve as a jejunostomy tube, e.g., the first lumen is shorter in length than the second lumen. The sealing member is located on the elongated member and is arranged to be activated to seal the interface between the stoma and the distal portion of the elongated member. The first lumen has a distal end and at least one port adjacent the distal end of it. The second lumen has a distal end and at least one port adjacent the distal end of it.

In accordance with one preferred embodiment of the invention, the device includes two access ports, each of which is arranged to be coupled to a respective tube and which extend generally parallel to the longitudinal axis of the proximal portion of the elongated member. The access ports are arranged to provide communication to respective ones of the first and second lumens. The access ports can each be of a different shape or may include respective visually distinctive indicia, e.g., text, graphics, either flat, embossed or debossed and/or color, associated with them, so that they can be readily distinguished from each other.

In accordance with another preferred embodiment of the invention, at least some portions of the device which may engage the tissue of the being are provided with an anti-granuloma composition comprising an anti-granuloma agent, e.g., the retaining member includes a lower surface from which the proximal portion of the elongated member projects, and wherein the anti-granuloma composition is provided in the form of a disk for disposition on that lower surface and about said proximal portion of the elongated member and/or a sleeve for disposition about the proximal portion of the elongated member immediately adjacent the lower surface.

In accordance with another preferred embodiment of the invention, there is provided a member for use with a medical device for long-duration residence extending through an artificial opening in the body of a being. The medical device comprises an elongated member arranged to be extended through the opening from the skin of the being. The member is arranged to be located contiguous with at least some portions of the medical device, which may engage the tissue of the being at the opening and comprises an anti-granuloma composition.

In accordance with another preferred embodiment of the invention, there is provided an improvement in a process for providing an artificial channel across a tissue of a being, comprising providing an elongated member through the tissue, the improvement wherein the elongated member is provided with a coating comprising an anti-granuloma composition effective to prevent and/or treat granulomas.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

This invention is directed to a combination device for gastrostomy or jejunostomy usage providing a smooth delivery of food or medication to a patient contemporary with gastric decompression.

Additionally, the inventor has discovered that by incorporating an anti-inflammatory agent, e.g., a steroid, into the materials from which at least a part of the device for facilitating access to an internal cavity of an organism is manufactured, granulation tissue can be treated or prevented. The invention is not limited to the treatment of children or humans in general, but can also be employed for veterinary and animal husbandry purposes. Similarly, the invention is not limited to gastrostomy or jejunostomy usage, but can also be employed with other implantable devices in general, e.g., tracheostomy tubes and pharyngostomy tubes.

Figure 1:
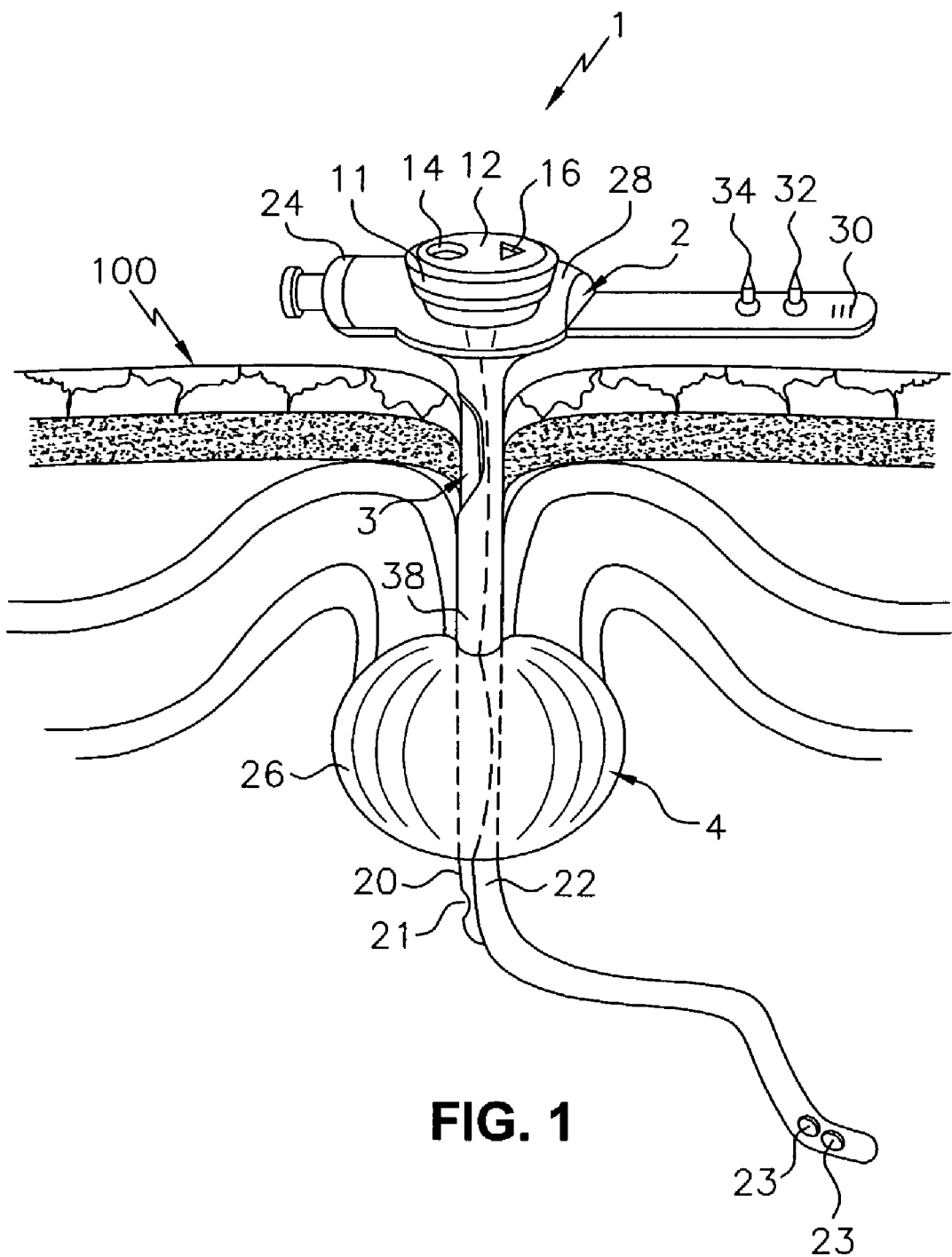
FIG. 1 is an isometric view, partially in section, of one exemplary embodiment of a low profile gastrostomy/jejunostomy device constructed in accordance with the teachings of the present invention shown in place within the body of a patient, e.g., a child, and also showing the use of optional anti-granuloma coverings constructed in accordance with another aspect of the present invention.

In FIG. 1 there is shown at 1 one exemplary embodiment of a gastrostomy/jejunostomy device constructed in accordance with one aspect of this invention. The device basically comprises a retaining member 2, an elongated member 3 and a sealing member 4. The device 1 present a low external profile and is constructed so that it can be used for both gastric access and jejunal access. The term "access" as it applies to the gastrostomy/jejunostomy device means a channel for either delivery of a substance, such as food, liquid, and/or medication, as well as a channel for allowing an exit for gases to provide a decompression.

Figure 6:
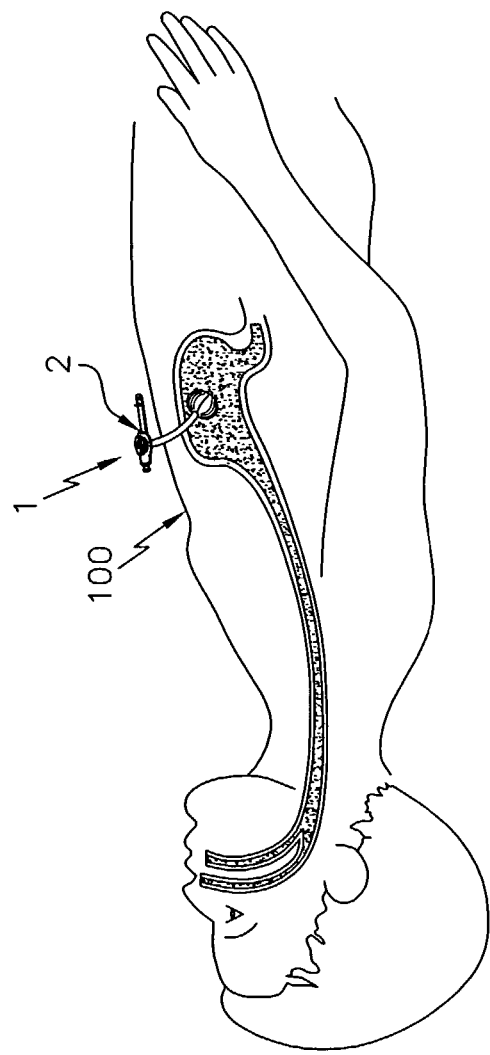
FIG. 6 is an illustration of a patient, partially in section, showing the use of the subject invention.

The term "low profile" as it applies to the gastrostomy/jejunostomy device means a skin-level device or a device which projects outward only a few inches from the patient's skin when it is in place. A low profile device preferably extends outwardly from the patient's skin less than 6 inches (15 cm), more preferably less than 4 inches (10 cm), even more preferably less than 2 inches (5 cm). The device 1 of the subject invention exhibits a very low profile since its retaining member 2 extends less than an inch from the patient's skin when the device is in place, such as shown in FIG. 6.

The details of the elongated member 3 will be discussed later. Suffice it to state that the elongated member 3 is connected to and projects downward from the under (lower) surface of the retaining member 2. The elongated member 3 includes a pair of conduits or lumens (to be described later) for insertion through a stoma into the patient's body 100 as is conventional practice. The elongated member is flexible and tapers downward in the distal direction from its maximum width or diameter, e.g., 18 French, at its proximal end (the point at which it merges with the retaining member 2).

The retaining member basically comprises a housing including a top plate 11 forming the top surface of the device 1. A button 12 is provided in the top plate 11. The top button 12 includes a gastrostomy access port 14 for gastric access and a jejunostomy access port 16 for jejunal access.

The gastrostomy access port 14 can have a first shape and the jejunostomy access port 16 can have a second shape. The first shape can be different than the second shape to remind the user which port is being accessed. For example, the gastrostomy access port 14 can have a round shape and the jejunostomy access port 16 can have a triangular shape, such as shown in FIG. 1. Alternatively, the gastrostomy access port 14 can have a triangular shape and the jejunostomy access port 16 can have a circular shape (not shown). It will be appreciated that alternative shapes can be used for the gastrostomy access port 14 and the jejunostomy access port 16. Respectively shaped connectors and associated tubings (not shown) are arranged to be releasably secured to the gastrostomy access port 14 and the jejunostomy access port 16 for receiving desired fluids and/or allowing gases to vent from the patient's body 100.

As mentioned earlier, the elongated member 3 includes a pair of conduits or lumens. In particular, the gastrostomy access port 14 is coupled to a conduit or lumen 20 extending down a portion of the length of the elongated member 3. The length of the conduit or lumen 20 is appropriate for gastric access. A gastric or "G" opening(s) 21 extends through the wall of the elongated member and is in communication with the interior of the conduit or lumen 20 adjacent the distal end thereof to provide gastric access. The jejunostomy access port 16 is coupled to a conduit or lumen 22 extending down the entire length of the elongated member 3. The length of the conduit or lumen 22 is appropriate for jejunal access. Two jejunal or "J" openings 23 extend through the wall of the elongated member 3 and are in communication with the interior of the conduit or lumen 22 adjacent the distal end thereof to provide jejunal access. The two lumens 20 and 22 are separate from each other but extend parallel to each other, e.g., they are separated by a longitudinally extending wall (not shown). The conduit 20 and conduit 22 preferably each have a predetermined length and diameter for providing appropriate gastrostomy and jejunostomy access.

In order to seal the periphery of the stoma about the elongated member 3, the device includes the heretofore-identified sealing member 4. In particular, that member comprises a conventional inflatable balloon 26. The retaining member 2 includes a balloon port 24 coupled to the balloon 26 to effect its inflation. When the balloon is inflated, it serves to hold the device 10 in place and prevent leakage of gastric contents via patient's stoma. A pair of anti-reflux valves 28 is provided in the retaining member and each is coupled to an associated access port to prevent reflux from the device 1.

In order to seal the two access ports 14 and 16, when either or both are desired to be sealed, the retaining member 2 includes an elongated strap 30 projecting outward therefrom, generally parallel to the skin of the patient. The strap is preferably flexible and includes on its upper surface a pair of projecting plugs 32 and 34. The plug 32 is shaped to be received within and to seal the G access port 14, while the plug 34 is shaped to be received within and to seal the J access port 16.

In order to treat, prevent or at least minimize the chance that granuloma tissue will occur at the situs of the stoma through which the elongated member of the device 1 projects and along the site of a contact of the device and the tissue, particularly in cases of long-term usage, the device 1 may be manufactured from biodegradable polymers combined with an anti-granuloma agent, which is controllably released and thus provides a site-specific delivery of the anti-granuloma agent to a site of a contact of the device of the present invention with the tissue.

Alternatively, the device 1 may include a covering providing an anti-granuloma composition comprising at least one anti-granuloma agent mixed with at least one controlled release agent, the anti-granuloma composition capable of controlled release of the anti-granuloma agent and thus providing a site-specific delivery of the anti-granuloma agent to a site of a contact of the device of the present invention with the tissue.

The inventor has discovered that by incorporating an anti-granuloma agent into the materials from which at least a part of device for facilitating access to an internal cavity of an organism is manufactured, granulation tissue can be effectively treated or prevented.

A granuloma is a focal area of granulomatous inflammation. For detailed discussion of origin and morphology of granulomas see Robbins Pathologic Basis of Disease by Robbins et al., 5th Edition (1994), pp 81–83. One type of granuloma is called a foreign body granuloma and is incited by relatively inert foreign bodies.

"Anti-granuloma agents" as used herein are agents that can treat or prevent formation of granulomas tissue adjacent to the site of a device's access to an internal cavity of an organism. Anti-granuloma agents can be selected from a broad category of organic and inorganic, synthetic and natural materials, and derivatives thereof, which can treat or prevent formation of granulomas. Such materials include but are not limited to synthetic organic compounds, peptides, polypeptides, proteins, lipids, sugars, carbohydrates, certain RNA and DNA, and fatty acids, as well metabolites and derivatives of each. Anti-granuloma agents may also take the form of, or be available from, genetic material, viruses, prokaryotic, or eukaryotic cells. Anti-granuloma agents can be in various forms, such as unchanged molecules, components of molecular complexes, or pharmacologically acceptable salts or simple derivatives such as esters, ethers, and amides. Anti-granuloma agents may be derived from viral, microbial, fungal, plant, insect, fish, and other vertebrate sources.

Exemplary anti-granuloma agents include, but are not limited to, anti-inflammatory agents such as steroidal drugs, for example corticosteroids such as triamcinolone acetonide (9-fluoro-11β, 16α, 17, 21-tetrahydroxypregna-1, 4-diene-3, 20-dione cyclic 16, 17-acetal with acetone ($C_{24}H_{31}FO_6$)), triamcinolone hexacetonide, dexamethasone (9-alpha-fluoro-16-alpha-methylprednisolone), methyl prednisone, triamcoline (fluoroxyprednilisone), hydrocortisone (17-hydroxycorticosterone), and analogs thereof, and non-steroidal drugs, for example ketoprofin (2-(3-benzophenyl)propionic acid), cyclosporin, naproxin (D-2-(6-methoxy-2-naphthyl) propionic acid), and Ibuprofen (4-isobutyl-alpha-methylphenyl acetic acid). The preferred anti-granuloma agent is triamcinolone acetonide.

Other exemplary anti-granuloma agents include neovascularization agents such as cytokines. Cytokines are growth factors such as transforming growth factor alpha (TGFA), epidermal growth factor (EGF), vascular endothelial growth factor (VEGF), and anti-transforming growth factor beta (TGFB). TGFA suppresses collagen synthesis and stimulates angiogenesis. It has been shown that epidermal growth factor tethered to a solid substrate retains significant mobility and an active conformation. VEGF stimulate angiogenesis, and is advantageous because it selectively promotes proliferation of endothelial cells and not fibroblasts or collagen synthesis, in contrast to other angiogenic factors. In addition to promoting would healing, the improved blood flow resulting from the presence of neovascularization agents should also improve the accuracy of sensor measurements.

Other anti-granuloma agents include neutralizing antibodies including, for example, anti-transforming growth factor beta antibody (anti-TGFB); anti-TGFB receptor antibody; and anti-fibroblast antibody (anti-CD44). Anti-TGFB antibody has been shown to inhibit fibroblast proliferation, and hence inhibit fibrosis. Because of the importance of TGFB in fibrosis, anti-TGFB receptor antibodies inhibit fibrosis by blocking TGFB activation of fibroblasts. Recent studies have demonstrated that anti-CD44 antibody induces programmed cell death (apoptosis) in fibroblasts in vitro. Other anti-proliferative agents include Mitomicyin C, which inhibits fibroblast proliferation under certain circumstances, such as after vascularization has occurred.

In one embodiment of the present invention, the anti-granuloma agent is selected from the group consisting of steroids, antibiotics, anti-fungals, anti-inflammatories, anesthetics, vasoconstrictors, therapeutic drugs and therapeutic compositions.

In certain embodiments of the present invention, at least one anti-granuloma agent is mixed with at least one controlled release agent to form an anti-granuloma composition capable of controlled release of the anti-granuloma agent and thus providing a site-specific delivery of the anti-granuloma agent to a site of a contact of the device of the present invention with the tissue.

Controlled release agents are known in the art, and most commonly comprise biodegradable linkages or forms, which release the anti-granuloma agent upon degradation at the site of contact with a tissue. Exemplary controlled release agents include but are not limited to biodegradable polymers, nanoparticles, and controlled release vesicles such as liposomes and microspheres. Since many controlled release delivery systems can be manufactured to provide different release rates under the same conditions, in one embodiment, a single anti-granuloma agent may be provided at different release rates, to achieve a specific release profile. In another embodiment, the availability of a plurality of anti-granuloma agents is regulated by the different release rates of the delivery systems.

In certain embodiments of the present invention, at least one anti-granuloma agent is mixed with at least one biodegradable polymer to form an anti-granuloma composition and thus providing a site-specific delivery of the anti-granuloma agent to a site of a contact of the device of the present invention with the tissue at a rate of degradation of the biodegradable polymer efficient to cure or prevent the formation of granulomas.

As used herein, the term "biodegradable" refers to materials, which are enzymatically or chemically degraded in vivo into simpler, and preferably innocuous chemical species.

The biodegradable polymers are generally biocompatible, that is, physiologically tolerated and not the source of adverse local or systemic responses.

The general criteria for selecting a polymer for use in a body as a biomaterial is to match the mechanical properties and the time of degradation to the needs of the application. For example, if the device is left in a body for at least 12 weeks, the composition including the biodegradable polymer and the anti-granuloma agent can be designed to degrade and release the anti-granuloma agent within at least 12 weeks.

The suitable polymer for a particular application would be configured so that it does not invoke an inflammatory or toxic response, is metabolized in the body after fulfilling its purpose, leaving no trace, is easily processable into the final product form, demonstrates acceptable shelf life, and is easily sterilized.

Biodegradable polymers can be either natural or synthetic. An example of a natural polymer is a polysaccharide. Synthetic polymers include poly(lactic acid) (PLA), poly (glycolic acid) (PGA) and co-polymers of PLA and PGA such as poly(lactide-co-glycolide) (PLGA), polyorthoesters, polyanhydrides, polyphosphazene, polycaprolactone, poly-hydroxybutyrate, p-dioxanone, poly(dioxanone)(polyetherester), blends and copolymers thereof. Preferred biodegradable polymer is a member selected from the group consisting of polyglycolide (PGA), polylactide (PLA) and isomers thereof, poly(-caprolactone), poly(dioxanone)(polyether-ester), and poly(lactide-co-glycolide) (PLGA).

For anti-granuloma agents that are hydrolytically unstable, hydrophobic polymers that degrade by surface erosion rather than by bulk hydrolytic degradation should be used. Preferred polymers are selected from the group consisting of polyanhydrides and the polyorthoesters.

PLA polymers are usually prepared from the cyclic esters of lactic acids. Both L(+) and D(-) forms of lactic acid can be used to prepare the PLA polymers, as well as the optically inactive DL-lactic acid mixture of mixtures of D(-) and L(+) lactic acids. Methods of preparing polylactides are well documented in the patent literature. The following U.S. patents describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; U.S. Pat. No. 2,683,136 to Higgins; and U.S. Pat. No. 3,531,561 to Trehu.

PGA is the homopolymer of glycolic acid (hydroxyacetic acid). In the conversion of glycolic acid to poly(glycolic acid), it is initially reacted with itself to form the cyclic ester glycolide, which in the presence of heat and a catalyst is converted to a high molecular weight linear-chain polymer. PGA polymers and their properties are described in more detail in "Cyanamid Research Develops World's First Synthetic Absorbable Suture", Chemistry and Industry, 905 (1970).

Both the release of the incorporated anti-granuloma agent and the bioerosion of the matrix (the polymer) are related to the molecular weights of PLA, PGA or PLGA. The higher molecular weights (e.g., weight average molecular weights of 90,000 or higher) result in polymer matrices which retain their structural integrity for longer periods of time, while lower molecular weights (weight average molecular weights of 30,000 or less) result in both slower release and shorter matrix lives.

In addition, degradation times can be adjusted from days to years according to the degree of hydrophobicity of the selected monomers and chemical stability of the polymer backbone. See Middleton et al., Synthetic Biodegradable Polymers as Medical Devices, Medical Plastics and Biomaterials Magazine, (March 1998).

In certain embodiments of the present invention, association of the anti-granuloma agent with the biodegradable polymer may be by physical means, i.e., entrapment within the polymer layer, or by covalent attachment within the biodegradable polymer layer and/or at the surface of the biodegradable polymer layer, thereby forming an anti-granuloma composition capable of controlled release of the anti-granuloma agent. Entrapment may occur at the time the layer is formed, or subsequently, i.e., by absorption of the anti-granuloma agent into the formed layer. The anti-granuloma composition comprising at least one biodegradable polymer and at least one anti-granuloma agent can be prepared by methods known in the art.

The anti-granuloma composition of the present invention can be provided as a coating on at least a portion of the device of the present invention that engages the skin and/or tissue of the patient to cure, prevent or at least lessen the chances of a granuloma to be produced.

As used herein, the term "coating" or "coverings" is inclusive of a permanent or removable surface or a layer comprising the anti-granuloma composition and capable of controlled release of the anti-granuloma agent from the anti-granuloma composition. A removable coating can be provided in the form of a disk, a sleeve with or without a slit, as well as a sheet as described in details below.

It is to be understood that the term "layer" as used herein is inclusive of blocks, patches, semicircles, and other geometries without limitation. While the biodegradable polymer may assume almost any geometry, layers are generally preferred, being in the range from about 0.05 to about 5 mm thick, preferably from about 0.1 to about 1 mm thick.

The permanent coating can be made by methods known in the art such as coacervation, lamination, spray coating, etc. The removable coating can also be made by known methods such as, for example, injection molding.

To prepare the coating of the present invention, polymerization methods known in the art may be used, depending on the materials from which the device of the present invention is manufactured. Thus, for devices capable of tolerating increased temperatures, polymerization may be initiated by heat in the presence of initiator such as azobisisobutyronitrile (AIBN). Photoinitiation by UV light may be used in the presence of initiators such as benzoin or benzil, and by visible light in the presence of initiators such as Eosin. Binding of the coating to the device may be by mechanical forces, as the sheath around the device formed during preparation of the coating shrinks considerably during polymerization or by using a binder.

In still another embodiment, the anti-granuloma agents are associated with a biodegradable polymer layer, which is generated by supramolecular self-assembly using, for example, substances such as NAFION/$Fe^{3+}$ complex, mussel adhesive protein (MAP), humic acids and/or a poly (anion)/poly(cation) technology as described in U.S. Pat. No. 6,497,729 to Moussy et al.

In certain embodiments of the present invention, at least one anti-granuloma agent is mixed with at least one microsphere to form an anti-granuloma composition capable of controlled release of the anti-granuloma agent and thus providing a site-specific delivery of the anti-granuloma agent to a site of a contact of the device of the present invention with the tissue.

Microspheres are micron-sized spherical articles, typically prepared using natural or synthetic polymers, and have been demonstrated to effectively deliver a number of drugs, including dexamethasone and various proteins. To maximize control of the diverse and dynamic processes involved in inflammation, mixtures of microspheres comprising different anti-granuloma agents may be used in combination. Additionally, microspheres can be manufactured so as to release the various anti-granuloma agents at different rates, to control the different phases of the tissue reaction. Microspheres having diameters of greater than about 10 microns are presently preferred. The microspheres may be covalently attached to the device or be physically entrapped within the biodegradable polymer or a hydrogel as described in Moussy et al.

Coupling to the biodegradable polymer or a hydrogel is by incorporation of different functional surfactants onto the surface of the microspheres.

Microsphere delivery systems may be encapsulating, having the anti-granuloma agent incorporated into the center, or have the anti-granuloma agent dispersed throughout the polymer matrix. Each microsphere is optimized for formulation method, release rate, and dosage of specific anti-granuloma agents. Co-polymer ratio, particle size and drug loading are varied to achieve desired release rates of the anti-granuloma agents. Since small microspheres are likely to be phagocytosed and removed from the site, preferred microspheres have diameters in the range from about 10 to about 100 microns. The method described by M. Tsung and D. J. Burgess, in J. Pharm., Vol. 86, p. 603 (1997) may be used for particle sizing. SEM, TEM, and optical microscopy are used to determine microsphere size, shape, surface characteristics, and internal structure. Nanoparticles with diameters less than 10 microns are also useful.

A number of polymers are suitable for use in slow release microspheres, including but not being limited to proteins, as disclosed in U.S. Pat. No. 5,271,961, polyorthoesters, poly (lactic acid), poly(gycolic acid) polyahydrides, polyphosphazene, polycaprolactone, polyhydroxybutyrate and combinations thereof. A preferred polymer is poly(lactic-glycolic acid) (PLGA). PLGA is bioactive, does not itself result in any significant inflammatory reaction, can be manufactured to have different release rates, and is suitable for use with a variety of both water-soluble and water-insoluble drugs. PLGA microsphere preparations are commercially available under the trade name LUPRON-DEPOT and are approved for use by the Federal Drug Administration (FDA) for parenteral administration. Ratio of glycolic acid to lactic acid, particle size, molecular weight of the polymer and drug loading are varied to achieve desired release rates of the tissue response modifiers.

Modification of the PLGA microsphere surface by tresylation allows covalent attachment of the microsphere to the hydroxyl groups of the hydrogel. Attachment of polyethyleneamine or polyvinyl alcohol to the microsphere surface occurs by addition of these elements during microsphere preparation. These elements allow coupling to the interactive surface of hydrogels. Copolymerization of PLGA with a small amount of glutamic acid (approximately 5%) also allows coupling of the microspheres with the hydrogels.

Coating or modifying the surface of the PLGA microspheres also allows adjustment of biocompatibility, biodegradation, and release rates. Glutamic acid imparts a negative charge on the surface of the microspheres, allowing self-assembly with the polypeptides. As an alternative, polyethyleneamine, phosphatidic acid or phosphatidylinositol attached to the microsphere surface imparts positive, negative, and negative charges, respectively. These elements become attached to the microsphere surface by incorporating them during microsphere preparation.

Preparation of microspheres comprising water-insoluble anti-granuloma agents such as dexamethasone relies on the hydrophobicity of these molecules. A simple oil/water emulsion technique is used, wherein the dexamethasone, e.g., is entrapped within the internal oil phase (PLGA/methylene chloride) of the emulsion and hence within the microspheres following solvent evaporation, as described by C. Grandfils, et al., in J. Biomedical Materials Research, Vol. 26, p. 467 (1992). In order to increase dexamethasone content within the microspheres, dexamethasone partitioning into the aqueous phase is reduced by changing the oil phase, e.g. a methylene chloride/acetone mixture is used in place of methylene chloride.

For hydrophilic anti-granulomas factors such as VEGF and other polypeptides, a modification of a multiple emulsion technique described by Toguchi et al. in J. Pharm. Sci., Vol. 83, p. 636 (1994) is used, since polypeptides are generally water soluble and therefore must be entrapped in the internal water phase of a water/oil/water emulsion. This method ensures polypeptide entrapment within the PLGA microspheres following solvent evaporation. During entrapment of VEGF, addition of phosphatidyl choline (PC) as a surfactant and reduction in the temperature of preparation to 30° C. results in improved emulsion stability and hence VEGF content and activity following entrapment in the microspheres. Sucralfate, a protease inhibitor, may be added to preserve polypeptide activity in vivo. Rat serum albumin may also be added to facilitate release rates.

In addition to the above-described methods, general methods for the manufacture of the present combination of an anti-granuloma coating with the device will depend on the nature of the device, the nature of the one more biodegradable polymer layers, and the nature of the anti-granuloma agents. The part of the device to be coated may be cast or coated with, or dipped or immersed into a solution of monomer, followed by polymerization onto the device. Alternatively, the device may be coated by melting, dipping, casting, or coating with the polymerized monomer, followed by removal of a solvent (if present). Self-assembly type polymer coatings are generally assembled directly on the surface of the device, optionally in-situ. The monomer or polymer solutions may comprise the anti-granuloma agent; thereby incorporating the anti-granuloma agent during deposition, or the anti-granuloma agent may be adsorbed into the layer after deposition, optionally in-situ, e.g., after the device has been inserted in a patient. The amount of the anti-granuloma agent incorporated in the anti-granuloma composition will vary depending on the particular type of anti-granuloma agent used, the desired therapeutic or prophylactic effect and the time-span over which anti-granuloma agent delivery is desired. Since a variety of devices in a variety of sizes and shapes may be fashioned for control of a variety of the anti-granuloma agents, the upper and lower limits will depend on the activity of the anti-granuloma agent(s) and the time span of release from the device desired in a particular application. The surface area of the device occupied by the anti-granuloma composition will also impact the amount of anti-granuloma agent in the composition. Thus, it is not practical to define a range for the therapeutically effective amount of the anti-granuloma agent to include herein.

Duration of action and dosage level are also adjustable, which is critical in controlling inflammation. Lower dosage levels are required for targeted delivery (as opposed to systemic administration), which lowers the cost of treatment.

Determination of the precise anti-granuloma coverings/device configuration and the quantity and form of the anti-granuloma agent effective to prevent/control the formation of granulomas at the site of implantation is within the abilities of one of ordinary skill in the art, and will depend on the particular site of access, the length of time that the device is intended to remain in the body, and the device itself.

Figure 2:
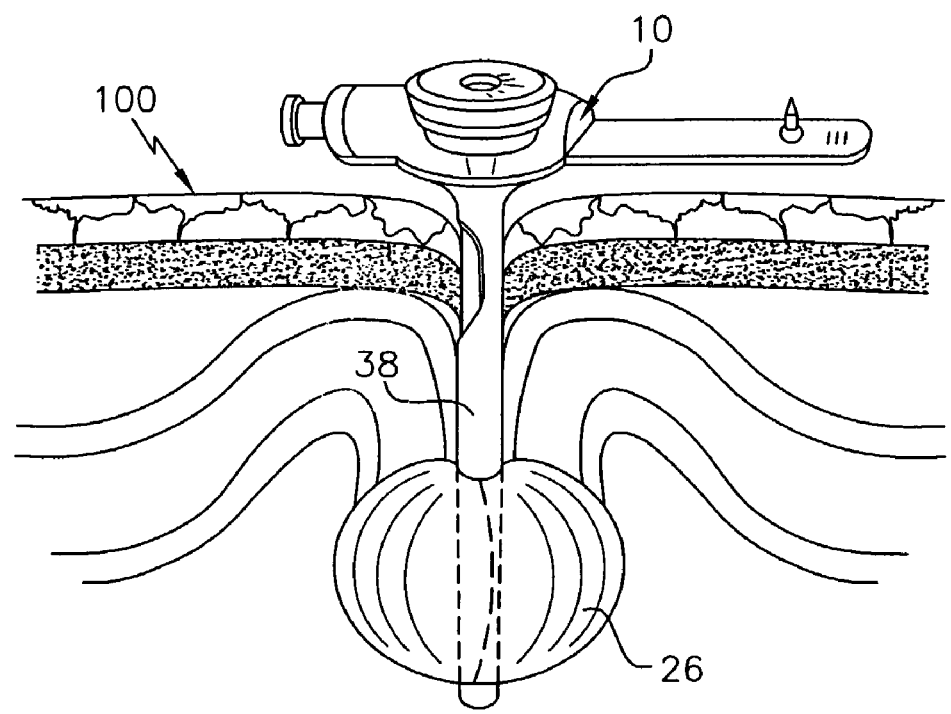
FIG. 2 is an isometric view, partially in section, of a conventional low profile gastrostomy/jejunostomy device including anti-granuloma coverings constructed in accordance with another aspect of the present invention.
Figure 3:
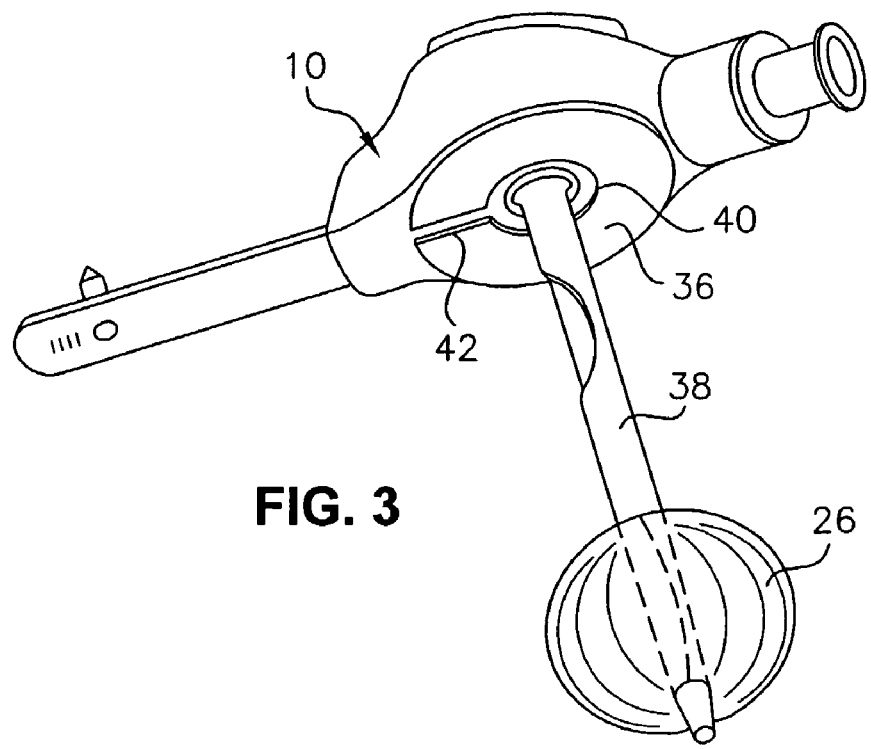
FIG. 3 is an isometric view, partially in section, of the embodiment of FIG. 2, but showing the underside surface of the device and the anti-granuloma coverings.

In certain embodiments of the present invention, the anti-granuloma composition can be provided as a coating on the underside of the retaining member 2 of the device 1 and on the proximal end portion of the tubular member 3 of the device 1 so that those portions which will engage the skin and tissue of the patient contiguous with the stoma will prevent, treat or at least lessen the chances of producing a granuloma. Alternatively, the composition can be provided in the form of a covering comprising one or more components. In the embodiment shown in FIGS. 3–5 the anti-granuloma composition is in the form of two components, i.e., a disk 36, shown clearly in FIGS. 3 and 4, and a sleeve 38 shown clearly in FIGS. 3 and 5. These two components can be fabricated as a single component if desired. The disk and the sleeve can each have a slit in its surface to allow for easier placement onto the device as shown in FIG. 3. Coverings can also be in a form of a sheet and wrapped around the device (not shown). Moreover, the anti-granuloma agent can be provided as a coating or a covering on existing conventional devices as well as on devices constructed in accordance with this invention, e.g., the device of FIG. 1. To that end the disk 36 and sleeve 38 can be used on a device constructed in accordance with this invention, such as shown in FIG. 1, or can be used on any conventional device, e.g., as shown in FIGS. 2 and 3.

As can be seen in FIGS. 2–5, the disk 36 basically comprises a thin, generally planar circular member whose outer diameter is appropriate to cover the area of the patients skin contiguous with the stoma, and which has a central opening 40 whose diameter is just slightly larger than the outer diameter of the proximal end portion of the elongated member 3. The disk 36 may be adhesively secured to the undersurface of the retaining member 2, with the elongated member 3 extending through its central opening 40 as shown in FIG. 3, prior to its usage on the patient. It is also contemplated that the disk can be mounted on the underside of the retaining member some time after the device is in place. To that end, the disk 36 includes a slit 42 extending radially between the central opening 40 and the outer periphery of the disk 36. With this arrangement the disk 36 can be placed in position after the device is resident in the patient by merely deflating the balloon 26 to enable the device 1 to be retracted slightly out of the stoma, whereupon a slight space is created between the underside of the retaining member 2 and the patient's skin. The disk can then be slid in laterally onto the proximal portion of the elongated member by opening the slit 42. Once the disk is in place with the proximal portion of the elongated member extending through its central opening 40, the balloon 26 can be reinflated to bring the disk into engagement with the skin of the patient contiguous with the stoma.

Figure 5:
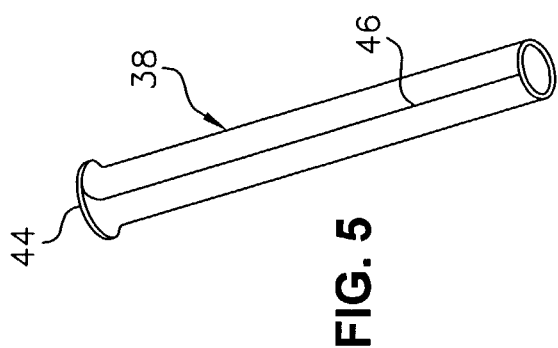
FIG. 5 is an isometric view of another exemplary embodiment, e.g., a sleeve, of an anti-granuloma covering of this invention.

The sleeve 38 basically comprises a tubular member of a thin walled construction whose inside diameter is just slightly larger than the outside diameter of the proximal end portion of the elongated member 3. Moreover, if the proximal end portion of the elongated member is flared outward in a curved surface where it merges with the underside surface of the retaining member, as is the case in the exemplary embodiment shown, the proximal end portion 44 of the sleeve is correspondingly shaped, as shown in FIG. 5. The sleeve's length is preferably sufficiently long to encompass the length of the elongated member 3 from the undersurface of the retaining member 2 to the proximal end of the balloon 26, but can be shorter if desired. Placement of the sleeve can be accomplished before the device is in place in the patient's body 100 by extending it over the distal end of the elongated member while the balloon is deflated and then sliding it in the proximal direction until it is at the position shown in FIGS. 1 and 3. If desired, the sleeve 38 may include a slit 46 (FIG. 5) extending longitudinally along its entire length to enable the sleeve to be placed on the proximal portion of the elongated member from a lateral direction. This feature enables the sleeve to be placed in position after the device 1 is residing in the patient. This can be accomplished by deflating the balloon 26 to enable the device 1 to be retracted out of the stoma to a distance where the proximal end of the balloon 26 is just visible. The sleeve 38 can then be slid in laterally onto the proximal portion of the elongated member 3 by opening the longitudinal slit 46. Once the sleeve is in place, the balloon 26 can be re-inflated to bring the sleeve 38 into engagement with the tissue of the stoma along the length thereof.

It is preferred that both the disk and sleeve be used if granuloma cure or prevention is desired, e.g., if the device is to be used for a sufficiently long time where a granuloma may be expected to occur. Use of both the disk and sleeve is not mandatory and either or none can be used, depending upon the application.

Operation of the device 1 will now be described. The device 1 is inserted through a stoma into the patient's body 100 as shown in FIG. 6, wherein lumen 22 is passed through the pyloric area of the stomach and into the patient's small intestine to deliver food, other liquids or semi-liquids through "J" openings 23. The lumen 20 remains in the stomach to provide access for gases e.g., gastric decompression through "G" opening(s) 21. The anti-granuloma agent(s) associated with the device are released at the site of the contact of the device with the tissue of the patient and thereby preventing the formation of granulomas, lessening the formation of granulomas, reducing the existing granulomas or curing the existing granulomas.

Figure 4:
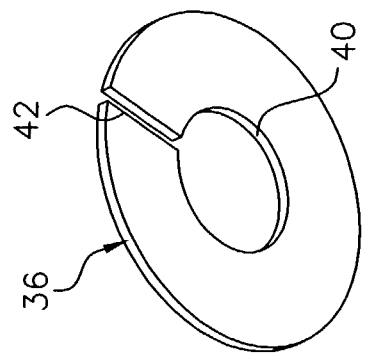
FIG. 4 is an isometric view of one exemplary embodiment, e.g., a disk, of an anti-granuloma covering of this invention.

The device 1 is usually left in the body for about 12 weeks or longer if necessary to allow the body of the patient to accommodate an access port through the stoma, establish the feeding, adjust to feeding conditions, and alleviate gastric discomfort. After this period, the device 1 can be removed and replaced with the conventional gastric device as shown in FIGS. 2 and 3 to provide the feeding thought the stomach without venting. The conventional gastric device can remain in the body as long as necessary. The conventional gastric device has anti-granuloma agent(s) associated with its surface in variety of ways e.g., as a covering, a sleeve (as shown in FIG. 5), a disk (as shown in FIG. 4), or materials from which the device is manufactured. The anti-granuloma agent(s) are released at the site of the contact of the device with the tissue of the patient and thereby preventing the formation, lessening the formation of granulomas, or curing the existing granulomas.

Also, any conventional device, which did not have anti-granuloma agents associated with it prior to its insertion into the patient's body, can be partially retracted from the body by deflating the balloon 26 (as shown in FIG. 2), fitted with appropriate covering as needed, and returned to its original position in the body.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

Without further elaboration the foregoing will so fully illustrate my invention that others may, by applying current or future knowledge, adopt the same for use under various conditions of service.

What is claimed is:

1. A combination device for gastrostomy or jejunostomy usage, said device comprising a retaining member, an elongated member and an activatable sealing member, said elongated member having a proximal portion connected to said retaining member and having a longitudinal axis, said elongated member comprising a first lumen and a second lumen, said sealing member being mounted on said elongated member, said retaining member being arranged to be located on skin of a being adjacent a stoma in an abdominal wall of the being and having a low profile with respect to the being's skin, said retaining member including a first access port and a second access port, each of said access ports extending generally parallel to said longitudinal axis and being arranged to have a respective tube coupled thereto, said elongated member being arranged to pass through the stoma so that said first lumen can serve as a gastrostomy tube and said second lumen can serve as a jejunostomy tube, said sealing member being located on said proximal portion of said elongated member and being arranged to seal an interface between the stoma and said proximal portion of said elongated member, said first lumen having a distal end and at least one first access port adjacent said distal end of said first lumen, said second lumen having a distal end and at least one second access port adjacent said distal end of said second lumen, each of said first and second access ports being arranged to provide communication to respective ones of said first and second lumens.

2. The combination device of claim 1, wherein each of said first and second access ports is of a different shape.

3. The combination device of claim 1, wherein each of said first and second access ports has respective distinctive indicia associated with it, whereupon said access ports can be readily distinguished from each other.

4. The combination device of claim 1, additionally comprising an anti-reflux valve.

5. The combination device of claim 1, wherein said first lumen is shorter in length than said second lumen.

6. The combination device of claim 1, wherein at least some portions of said device which may engage the tissue of the being at the stoma are provided with an anti-granuloma composition comprising at least one anti-granuloma agent.

7. The combination device of claim 6, wherein the anti-granuloma composition further comprises at least one controlled release agent.

8. The combination device of claim 7, wherein said at least one controlled release agent is at least one member selected from the group consisting of a biodegradable polymer, a nanoparticle, an emulsion, a liposome, and a microsphere.

9. The combination device of claim 8, wherein said biodegradable polymer is a member selected from the group consisting of polysaccharide, poly(lactic acid) and isomers thereof, poly(glycolic acid), poly(lactide-co-glycolide), polyorthoesters, polyanhydrides, polyphosphazene, polycaprolactone, polyhydroxybutyrate, p-dioxanone, poly(dioxanone)(polyether-ester), and blends and copolymers thereof.

10. The combination device of claim 9, wherein said biodegradable polymer is poly(lactic acid) and isomers thereof, poly(glycolic acid), or poly(lactide-co-glycolide).

11. The combination device of claim 6, wherein said retaining member includes a lower surface from which said proximal portion of said elongated member projects, and wherein said anti-granuloma composition is provided as a disk for disposition on said lower surface and about said proximal portion of said elongated member.

12. The combination device of claim 6, wherein said retaining member includes a lower surface from which said proximal portion of said elongated member projects, and wherein said anti-granuloma composition is provided as a sleeve for disposition about said proximal portion of said elongated member immediately adjacent said lower surface.

13. The combination device of claim 6, wherein said at least one anti-granuloma agent is at least one member selected from the group consisting of an anti-fibrotic agent, a steroidal anti-inflammatory agent, a non-steroidal anti-inflammatory agent, an anti-proliferative agent, a cytokine, a cytokine inhibitor, a growth factor, a vascular growth factor, a neutralizing antibody, a hormone, a cytotoxic agent, an antibiotic, an anti-fungal agent, an anesthetic agent, and a vasoconstrictor.

14. The combination device of claim 6, wherein said at least one anti-granuloma agent is at least one member selected from the group consisting of 9-fluoro-11β, 16α, 17, 21-tetrahydroxypregna-1, 4-diene-3, 20-dione cyclic 16, 17-acetal, 2-(3-benzophenyl)propionic acid, 9-alpha-fluoro-16-alpha-methylprednisolone, methyl prednisone, fluoroxyprednisolone, 17-hydroxycorticosterone, cyclosporin, D-2-(6-methoxy-2-naphthyl)propionic acid, 4-isobutyl-α-methylphenyl acetic acid, Mitomicyin C, transforming growth factor alpha, anti-transforming growth factor beta, epidermal growth factor, vascular endothelial growth factor, anti-transforming growth factor beta antibody, anti-fibroblast antibody, and anti-transforming growth factor beta receptor antibody.

15. The combination device of claim 6, wherein said at least one anti-granuloma agent is triamcinolone acetonide or triamcinolone hexacetonide.

16. The combination device of claim 1 further comprising a plug member for sealing said access ports.

17. A device for gastrostomy or jejunostomy usage, said device comprising a retaining member, an elongated member and an activatable sealing member, said elongated member having a proximal portion connected to said retaining member and having a longitudinal axis, said elongated member comprising at least one lumen, said sealing member being mounted on said elongated member, said retaining member being ranged to be located on skin of a being adjacent a stoma in an abdominal wall of the being and including an access port arranged to have a tube coupled thereto, said elongated member being arranged to pass through the stoma, said sealing member being located on said proximal portion of said elongated member and being arranged to seal an interface between the stoma and said proximal portion of said elongated member, at least some portions of said device which may engage a tissue of the being at the stoma are provided with an anti-granuloma composition comprising at least one anti-granuloma agent, wherein said retaining member includes a lower surface from which said proximal portion of said elongated member projects, and wherein said anti-granuloma composition is provided in the form of a disk for disposition on said lower surface and about said proximal portion of said elongated member.

18. The device of claim 17, wherein the anti-granuloma composition further comprises at least one controlled release agent.

19. The device of claim 18, wherein said at least one controlled release agent is a member selected from the group consisting of a biodegradable polymer, a nanoparticle, an emulsion, a liposome, and a microsphere.

20. The device of claim 19, wherein said biodegradable polymer is a member selected from the group consisting of a polysaccharide, poly(lactic acid) and isomers thereof, poly(glycolic acid), poly(lactide-co-glycolide), polyorthoesters, polyanhydrides, polyphosphazene, polycaprolactone, polyhydroxybutyrate, p-dioxanone, poly(dioxanone)(polyether-ester), and blends and copolymers thereof.

21. The device of claim 20, wherein said biodegradable polymer is poly(lactic acid) and isomers thereof, poly(glycolic acid), or poly(lactide-co-glycolide).

22. The device of claim 17, wherein said at least one anti-granuloma agent is a member selected from the group consisting of an anti-fibrotic agent, a steroidal anti-inflammatory agent, a non-steroidal anti-inflammatory agent, an anti-proliferative agent, cytokine, cytokine inhibitor, growth factor, vascular growth factor, neutralizing antibody, hormone, a cytotoxic agent, an antibiotic, an anti-fungal agent, an anesthetic agent, and a vasoconstrictor.

23. The device of claim 17, wherein said at least one anti-granuloma agent is a member selected from the group consisting of 9-fluoro-11β, 16α, 17, 21-tetrahydroxypregna-1, 4-diene-3, 20-dione cyclic 16, 17-acetal, 2-(3-benzophenyl)propionic acid, 9-alpha-fluoro-16-alpha-methylprednisolone, methyl prednisone, fluoroxyprednisolone, 17-hydroxycorticosterone, cyclosporin, D-2-(6-methoxy-2-naphthyl)propionic acid, 4-isobutyl-α-methylphenyl acetic acid, Mitomicyin C, transforming growth factor alpha, anti-transforming growth factor beta, epidermal growth factor, vascular endothelial growth factor, anti-transforming growth factor beta antibody, anti-fibroblast antibody, and anti-transforming growth factor beta receptor antibody.

24. The device of claim 17, wherein said at least one anti-granuloma agent is triamcinolone acetonide or triamcinolone hexacetonide.

25. The combination device of claim 17 additionally comprising a plug member for sealing said access ports.

26. A device for gastrostomy or jejunostomy usage, said device comprising a retaining member, an elongated member and an activatable sealing member, said elongated member having a proximal portion connected to said retaining member and having a longitudinal axis, said elongated member comprising at least one lumen, said sealing member being mounted on said elongated member, said retaining member being arranged to be located on skin of a being adjacent a stoma in an abdominal wall of the being and including an access port arranged to have a tube coupled thereto, said elongated member being arranged to pass through the stoma, said sealing member being located on said proximal portion of said elongated member and being arranged to seal an interface between the stoma and said proximal portion of said elongated member, at least some portions of said device which may engage a tissue of the being at the stoma are provided with an anti-granuloma composition comprising at least one anti-granuloma agent, wherein said retaining member includes a lower surface from which said proximal portion of said elongated member projects, and wherein said anti-granuloma composition is provided in the form of a sleeve for disposition about said proximal portion of said elongated member immediately adjacent said lower surface and wherein said sleeve is removable.

* * * * *